United States Patent
Trail et al.

(10) Patent No.: US 7,582,107 B2
(45) Date of Patent: Sep. 1, 2009

(54) COMPRESSION SCREW APPARATUSES, SYSTEMS AND METHODS

(75) Inventors: Ian A. Trail, Gtr Manchester (GB); Arnold-Peter C. Weiss, Barrington, RI (US); Eric S. Reindel, Encinitas, CA (US)

(73) Assignee: Integra Lifesciences Corporation, Plainsboro, NJ (US)

( * ) Notice: Subject to any disclaimer, the term of this patent is extended or adjusted under 35 U.S.C. 154(b) by 758 days.

(21) Appl. No.: 10/768,875

(22) Filed: Jan. 30, 2004

(65) Prior Publication Data

US 2004/0210227 A1 Oct. 21, 2004

Related U.S. Application Data

(60) Provisional application No. 60/444,565, filed on Feb. 3, 2003.

(51) Int. Cl.
*A61B 17/86* (2006.01)

(52) U.S. Cl. .................. 606/304; 606/316; 606/916

(58) Field of Classification Search .............. 606/61, 606/65–66, 72–73, 62–64, 67, 68, 90, 103, 606/246, 275, 300, 304, 316, 317–321, 328, 606/916, 86 A; 411/410, 412–413, 389, 411/374, 395, 397, 99, 263, 418, 426, 399, 411/416
See application file for complete search history.

(56) References Cited

U.S. PATENT DOCUMENTS

| | | | | |
|---|---|---|---|---|
| 1,576,413 A | * | 3/1926 | Cubitt | 411/263 |
| 3,051,169 A | * | 8/1962 | Gustaf-Bertil | 606/65 |
| 4,175,555 A | | 11/1979 | Herbert | |
| 4,432,358 A | * | 2/1984 | Fixel | 606/66 |
| 4,456,005 A | * | 6/1984 | Lichty | 606/60 |
| 4,640,271 A | | 2/1987 | Lower | |
| 4,772,286 A | | 9/1988 | Goble et al. | |
| 4,858,601 A | | 8/1989 | Glisson | |
| RE33,348 E | | 9/1990 | Lower | |
| 5,019,079 A | | 5/1991 | Ross | |
| 5,100,405 A | * | 3/1992 | McLaren | 606/72 |
| 5,167,664 A | * | 12/1992 | Hodorek | 606/73 |
| 5,201,733 A | | 4/1993 | Etheredge, III | |

(Continued)

OTHER PUBLICATIONS

Martin et al., "Central Tarsal Bone Factures in Six Horses: Report on the use of a Cannulated Compression Bone Screw," Equine Practice, vol. 14, No. 10, p. 23-27, (Nov./Dec. 1992).

(Continued)

*Primary Examiner*—Thomas C Barrett
*Assistant Examiner*—James L Swiger
(74) *Attorney, Agent, or Firm*—Jenkins, Wilson, Taylor & Hunt, P.A.

(57) ABSTRACT

Compression screw apparatuses, systems and methods are disclosed. In one embodiment, the compression screw includes a primary screw and a secondary screw. The primary screw includes an at least partially threaded leading portion and an at least partially threaded trailing portion. The secondary screw includes outer threads and has a central opening which is also threaded and adapted for being screwed onto and matingly engaging the trailing portion of the primary screw. Drivers can be used to rotatably control the primary screw and the secondary screw to cause compression of spaced-apart material, particularly for compression of bone fragments across a fracture line.

22 Claims, 8 Drawing Sheets

U.S. PATENT DOCUMENTS

| | | | |
|---|---|---|---|
| 5,217,462 A | | 6/1993 | Asnis et al. |
| 5,437,674 A | | 8/1995 | Worcel et al. |
| 5,498,265 A | | 3/1996 | Asnis et al. |
| 5,522,817 A | | 6/1996 | Sander et al. |
| 5,562,672 A | | 10/1996 | Huebner et al. |
| 5,584,629 A | * | 12/1996 | Bailey et al. ................. 411/178 |
| 5,725,529 A | * | 3/1998 | Nicholson et al. ............. 606/72 |
| 5,743,912 A | * | 4/1998 | Lahille et al. .................. 606/65 |
| 5,824,087 A | | 10/1998 | Aspden et al. |
| 5,827,285 A | * | 10/1998 | Bramlet ........................ 606/60 |
| 5,871,486 A | * | 2/1999 | Huebner et al. ................ 606/73 |
| 5,964,767 A | * | 10/1999 | Tapia et al. .................... 606/73 |
| 5,964,768 A | | 10/1999 | Huebner |
| 5,976,139 A | * | 11/1999 | Bramlet ........................ 606/66 |
| 5,993,450 A | | 11/1999 | Worcel |
| 5,997,541 A | | 12/1999 | Schenk |
| 6,030,162 A | | 2/2000 | Huebner |
| 6,048,343 A | * | 4/2000 | Mathis et al. .................. 606/72 |
| 6,048,344 A | | 4/2000 | Schenk |
| 6,139,552 A | | 10/2000 | Horiuchi |
| 6,187,008 B1 | | 2/2001 | Hamman |
| 6,224,606 B1 | | 5/2001 | Horiuchi |
| 6,299,615 B1 | | 10/2001 | Huebner |
| 6,306,140 B1 | | 10/2001 | Siddiqui |
| 6,319,254 B1 | * | 11/2001 | Giet et al. ...................... 606/73 |
| 6,413,260 B1 | * | 7/2002 | Berrevoets et al. ............ 606/73 |
| 6,458,134 B1 | * | 10/2002 | Songer et al. .................. 606/73 |
| 6,668,688 B2 | * | 12/2003 | Zhao et al. ..................... 81/439 |
| 2001/0049528 A1 | * | 12/2001 | Kubota ......................... 606/65 |

OTHER PUBLICATIONS

Sukul et al., "Biomechanical Measurements on Scaphoid Bone Screws in an Experimental Model," J. Biomechanics, vol. 23, No. 11, p. 1115-1121, (1990).

Notification of Transmittal of the International Search Report for International Application No. PCT/US04/02573 dated Dec. 17, 2004.

International Preliminary Examing Authority for PCT/US04/002573 dated May 9, 2005.

* cited by examiner

COMPRESSION SCREW APPARATUSES, SYSTEMS AND METHODS

RELATED APPLICATIONS

This application claims the benefit of U.S. Provisional Patent Application Ser. No. 60/444,565, filed Feb. 3, 2003, the disclosure of which is incorporated herein by reference in its entirety.

TECHNICAL FIELD

The subject matter disclosed herein relates generally to screw apparatuses and methods. More particularly, the present subject matter relates to screw apparatuses, systems and methods adapted for compression of suitable materials, particularly for compression of bone fragments across a fracture line or lines.

RELATED ART

A variety of screw apparatuses and methods have been developed for use in compression of various materials, particularly in the fields of orthopedics, podiatry, and chiropody. The prior art includes various types of screws for placement into bone for compressing bone fragments across a fracture line. As such, it is well known to utilize a screw for placement across a fracture or osteotomy in order to compress, or as is referred to in the field, fixate a fracture to promote the healing process.

Apparatuses and methods known in the medical field for reducing, fixing, and generally assisting the healing of fractured bones within the body typically require surgical intervention. Open reduction internal fixation (ORIF) is a method or technique developed for surgically repairing fractured bone generally involving the use of plates and screws or an intramedullary (IM) rod to stabilize fractured bone. Many complications typically exist, however, with this technique that prevent successful or optimal outcomes in all cases. Treatment methods can also significantly impact healing time, pain, and functional outcomes. Moreover, the necessity of reducing operative time is driven both by patient risk of infection, anesthetic complications, and health care costs. As a result, efforts are continuously made to improve surgical techniques and fixation devices to improve surgical outcomes, costs, and operative times.

Well-known factors that are typically significant in predicting the outcome of ORIF include:

1. Prominence of hardware, leading to soft tissue abrasions and general inflammation;
2. Accurate reduction of fracture site providing proper alignment in all degrees of freedom;
3. Reliable fixation that rigidly approximates bone segments during healing;
4. Production of adequate and predictable compression across fracture sites which provides impetus for improved healing;
5. Minimization of skin incision and exposure to patient; and
6. Minimal operative time.

Among the prior art, U.S. Pat. No. 4,175,555 to Herbert discloses a bone screw for providing compressive engagement which utilizes screw threads which are like-handed but of different pitch on its respective leading and trailing ends. In a preferred embodiment, the pitch of the leading screw thread exceeds that of the trailing screw thread.

U.S. Pat. No. 4,640,271, reissued as Reissue Pat. No. 33,348, to Lower discloses a bone screw having a shaft with a first set of fixed leading threads and a second set of trailing threads spaced apart from the first set of leading threads by an unthreaded central portion. The second set of trailing threads is provided on a sleeve which is freely slideable on the unthreaded shaft portion, and the sleeve has a smooth, inner cylindrical surface.

U.S. Pat. No. 5,019,079 to Ross discloses a unitary bone screw having proximal and distal threaded portions separated by a smooth, unthreaded intermediate section of a predetermined diameter. The proximal and distal threads are like-handed, but the distal threads are of a greater pitch than that of the proximal threads.

U.S. Pat. Nos. 5,217,462 and 5,498,265 both to Asnis et al. disclose a bone screw apparatus for providing compression across a fracture utilizing a threaded shank portion and a sleeve for mating in cooperation with the threaded shank portion. The threaded shank portion includes a distal threaded shank portion having a bone thread and a proximal threaded shank portion having a machine thread. The sleeve has a head and an innerthreading which threads with the proximal threaded shank portion. A connector means is provided which connects the sleeve with a proximal end of the proximal threaded shank portion and which permits the sleeve to move longitudinally with respect to the distal threaded shank portion after maximum implant length is reached. After the sleeve is assembled together with the threaded shank portion, the sleeve and the threaded shank portion are non-removably connected together such as by deforming some of the threads on the threaded shank portion to prevent disengagement of the sleeve therefrom. Removal of the implant from bone, therefore, requires removal of the implant as a whole.

U.S. Pat. No. 5,562,672 to Huebner discloses a bone screw apparatus having a continuously varying pitch including a tapered root portion having a relatively small diameter on a leading end of the screw and a larger trailing diameter. The pitch of the screw decreases between the leading and trailing ends thus causing the bone fragments in a fracture to be drawn together when the screw is installed across the bone fragments. The screw is a one-piece, headless, cannulated screw that utilizes a linearly varying diameter from its leading tip to its trailing base portion, and a thread pitch that varies from large at the tip to small at the base portion.

U.S. Pat. No. 6,319,254 to Giet et al. discloses a cannulated bone screw for compressing bone utilizing a screw shank having a thread with a distal zone and a proximal zone, and a screw head for threading onto the screw shank and for cooperating with its proximal zone by internal tapping complimentary to the thread of the shank. The screw head has an outside thread at a pitch which is smaller than the pitch of the screw shank, and the distal zone and the proximal zone of the screw shank are separated by a central zone shaped to be inactive during screwing of the bone screw into bone so as to form a sliding zone for bone fragments to be put into compression. The threads on the leading screw are identical in diameter and pitch in both the leading and trailing portions.

Despite the prior art compression screw apparatuses and methods, room for improvement remains in the art for compression screw apparatuses, systems and methods for easily and effectively achieving compression for suitable materials, particularly for compression of bone fragments across a fracture line.

SUMMARY

The subject matter disclosed herein provides novel compression screw apparatuses, systems and methods for compressing suitable materials, particularly for compressing bone fragments across a fracture line. A primary screw is provided having a leading end and an opposite trailing end, the primary screw having a lead portion with an outer surface that is at least partially threaded and a trailing portion with an outer surface that is at least partially threaded. A secondary screw is utilized having an outer surface that is at least partially threaded. The secondary screw defines a central opening with an inner surface that is at least partially threaded and adapted for mating engagement onto the threaded trailing portion of the primary screw.

In one preferred embodiment, the bone screw apparatus is cannulated throughout its length to allow utilization with a suitable guide wire and cannulated tools for drilling and driving. The lead and pitch of the outerthreads on the secondary screw preferably are substantially the same as the lead and pitch of the threads on the outside of the leading portion of the primary screw. The lead of the threads on the inner surface of the central opening of the secondary screw can be larger than the lead of the threads on the outer surface of the secondary screw. The trailing portion of the primary screw can be tapered and the central opening of the secondary screw can be correspondingly tapered to screw onto the tapered trailing portion of primary screw.

During use to compress two spaced-apart materials such as bone fragments, holes can be pre-drilled for both the primary screw and the secondary screw, and a driver can be used to screw into place the primary screw across the fracture line, with or without the secondary screw already positioned on the primary screw. Once the primary screw is in place, a separate driver can be used to turn or rotate the secondary screw into place and to cause compression of the bone fragments even while the first driver is used to maintain the primary screw in place. Placement of the secondary screw can be completed such that no portion of it is above the level of the bone.

It is therefore an object to provide novel compression screw apparatuses, systems and methods which can easily and effectively be used to compress suitable materials, particularly for compression of bone fragments across a fracture line.

An object having been stated hereinabove, and which is achieved in whole or in party by the present subject matter, other objects will become evident as the description proceeds when taken in connection with the accompanying drawings as best described below.

DETAILED DESCRIPTION

As used herein, the terms set forth below have the following, associated definitions as known to those of skill in the art of screw apparatuses:

PITCH—The distance from one point on a screw thread to a corresponding point on the next thread, measured parallel to the long axis of the screw.

PITCH DIAMETER—On a straight screw thread, the diameter of an imaginary cylinder where the width of the thread and the width of the space between threads is equal. On a tapered screw thread, the diameter, at a given distance from a reference plane perpendicular to the axis of a imaginary cone, the surface of which would pass through the threads at such point as to make equal the width of the threads and the width of the spaces cut by the surface of the cone.

LEAD—The distance a screw thread advances on one rotational turn, measured parallel to the axis. On a single-thread screw the lead and the pitch are identical; on a double-thread screw the lead is twice the pitch; on a triple-thread screw the lead is three times the pitch.

MAJOR DIAMETER—The largest diameter of an external or internal thread.

MINOR DIAMETER—The smallest diameter of a thread.

ROOT—The surface of the thread corresponding to the minor diameter of an external thread and the major diameter of an internal thread. Also defined as the bottom surface joining the flanks of two adjacent threads.

Figure 1:
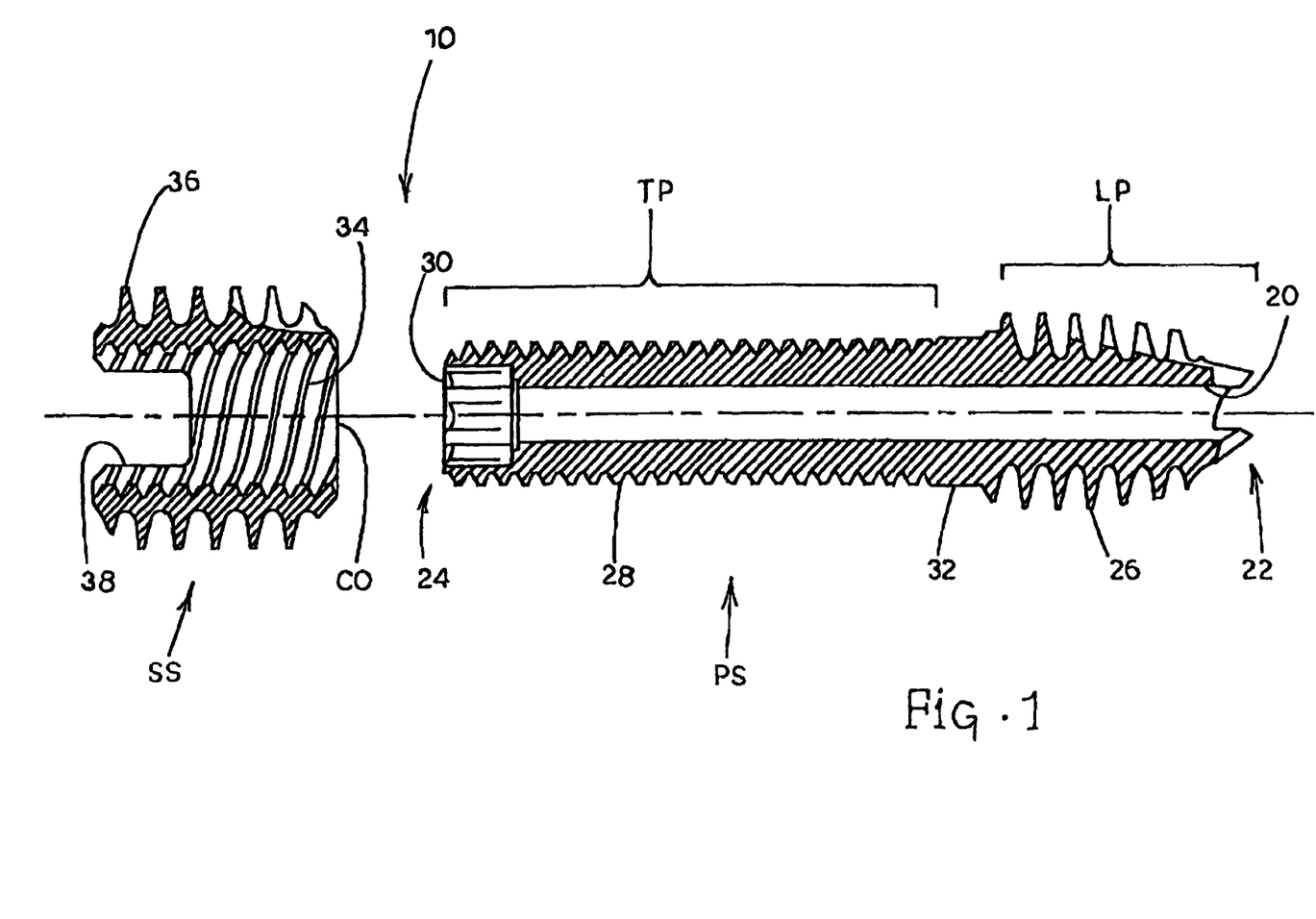
FIG. 1 of the drawings illustrates a side elevation, cross-section view of an embodiment of the compression screw apparatus.
Figure 2:
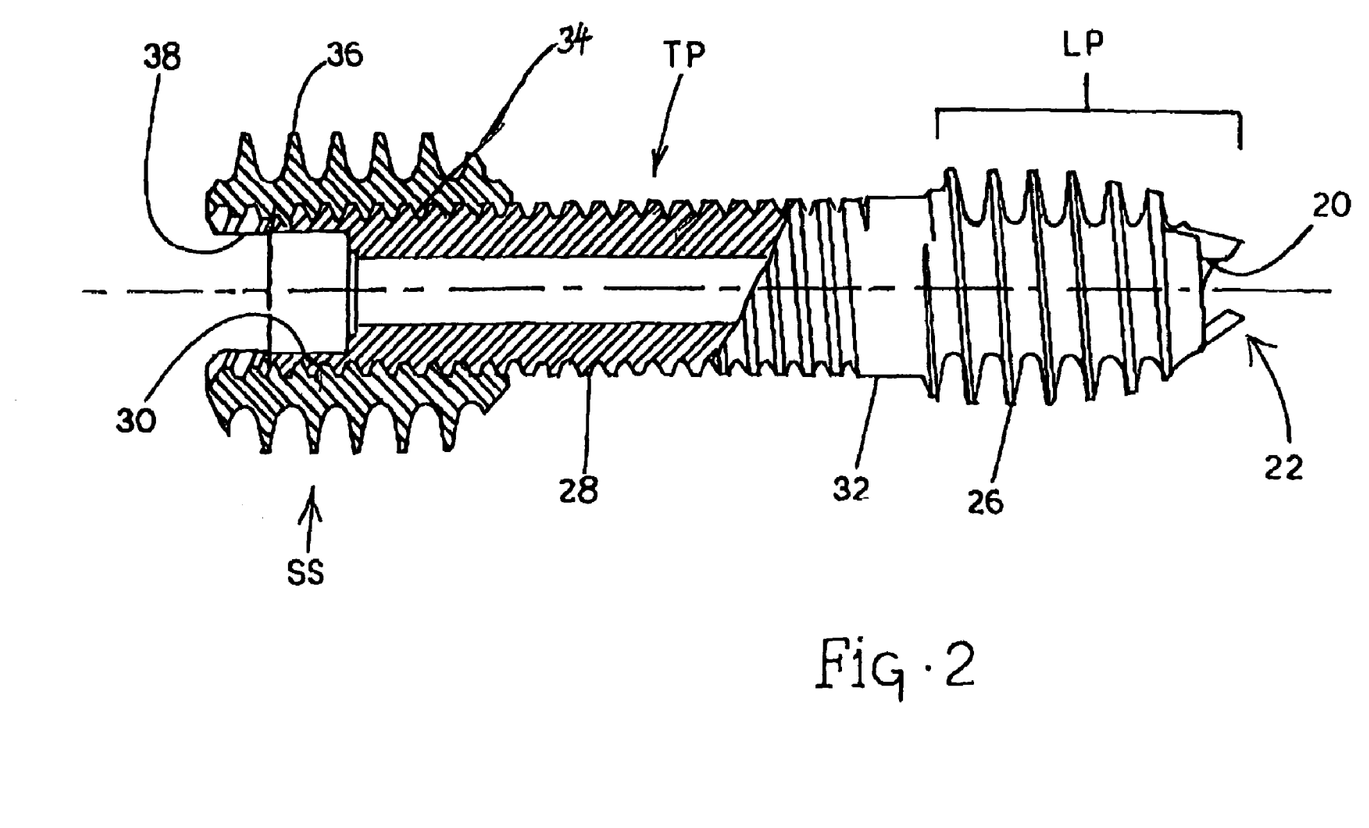
FIG. 2 of the drawings is a side elevation view in partial cross section illustrating the secondary screw partially screwed onto the primary screw.
Figure 3:
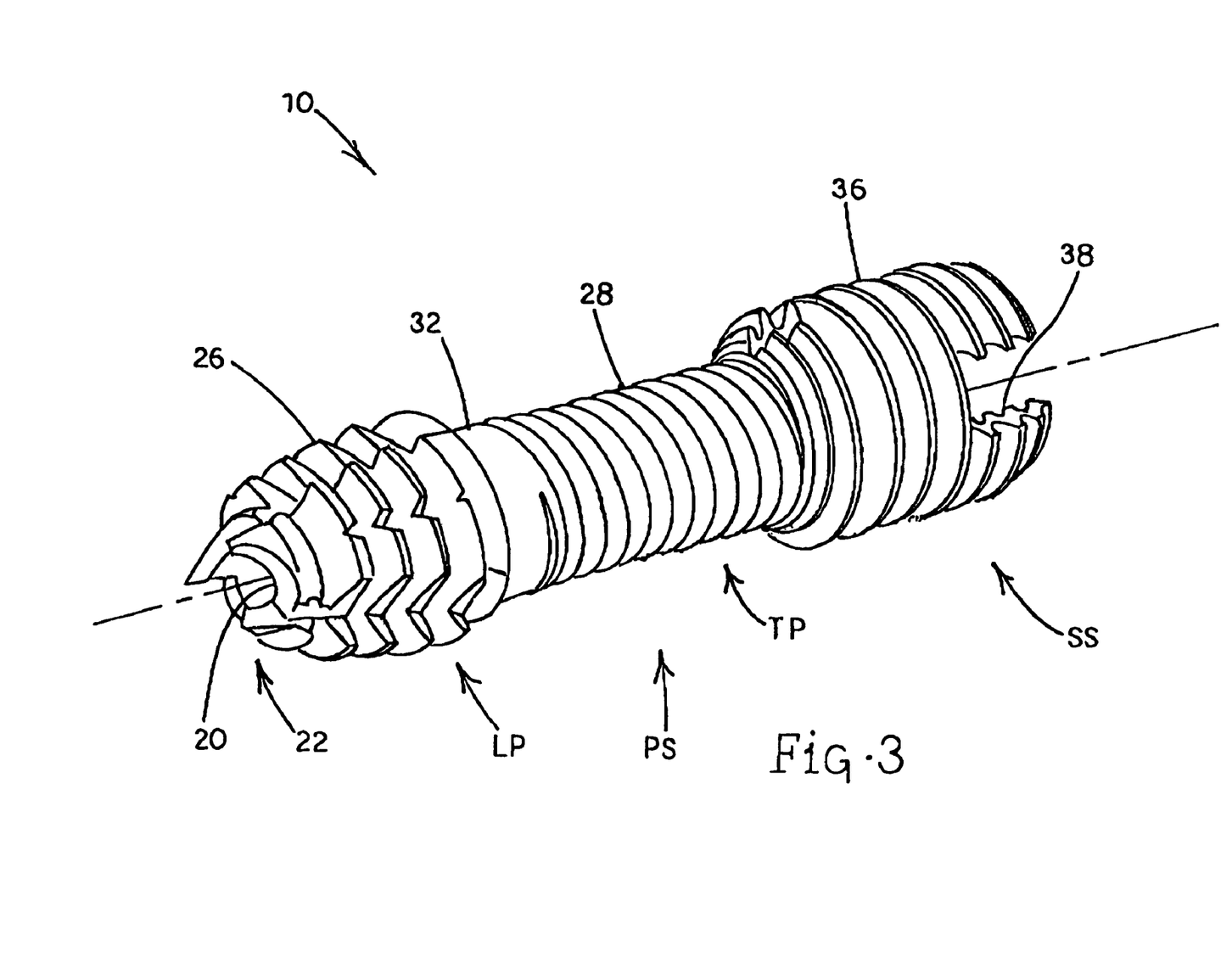
FIG. 3 of the drawings illustrates a perspective view of the compression screw apparatus.

Referring specifically to FIGS. 1,2 and 3 of the drawings, a compression screw apparatus generally designated 10 provided in accordance with the present invention is illustrated. As discussed above, compression screw apparatus 10 can be utilized for compression of any suitable materials, but is particularly suitable for compression of portions or fragments of bone across a fracture line. As shown, compression screw apparatus 10 comprises a primary screw, generally designated PS, and a secondary screw, generally designated SS, adapted to fit onto primary screw PS as further described herein. Primary screw PS and secondary screw SS are illustrated in FIG. 1 in a spaced-apart manner and in FIGS. 2 and 3 with secondary screw SS fitted at least partially onto primary screw PS. In one embodiment, secondary screw SS can be, but certainly does not have to be, at least one-half of the length of primary screw PS to provide a sufficient mating length.

Primary screw PS as shown in FIGS. 1 and 2 is at least generally cylindrical, disposed along a central axis and cannulated as it defines a longitudinal bore or passage 20 through its middle along its central axis. For smaller applications of compression screw 10, primary screw PS could be non-cannulated to provide increased strength. Primary screw PS has a leading end 22 which can be self-tapping for screwing into material such as bone, and a trailing end generally designated 24, on the end of primary screw PS opposite leading end 22. Primary screw PS includes a forward or lead portion designated LP, and a rear or trailing portion designated TP. The outer surface of lead portion LP is at least partially threaded, and preferably is substantially or entirely threaded such as with helical threads 26 shown best in FIGS. 1, 2, and 3. The outer surface of trailing portion TP is also at least partially threaded, and most preferably is substantially or entirely threaded such as with helical threads 28, also as best shown in FIGS. 1, 2, and 3. Threads 26 can spiral in the same direction or hand as threads 28.

Threads 26 can be tapered in design as shown, for example, in FIGS. 1, 2, and 3 where threads 26 taper at least partially to increase gradually in major diameter most or all of the distance from leading end 22 toward trailing portion TP. Such tapering can facilitate and encourage engagement of primary screw PS into material into which primary screw PS is being screwed. Threads 26 of leading portion LP can be courser in nature, have a deeper root, and be of a greater pitch than threads 28 of trailing portion TP. Additionally, the major diameter and pitch diameter of threads 26 of leading portion LP can be larger than that of threads 28 of trailing portion TP, as shown best in FIGS. 1 and 2, as the diameter of trailing portion TP is preferably larger than that of the major diameter of threads 26 of leading portion LP. It is envisioned in accordance with this invention that these relative configurations could change depending on the design preferred for various applications.

The lead of threads 26 can be of any suitable lead, such as for example single lead, double lead, or triple lead. When compression screw 10 is used for compressing bone, threads 26 are preferably cancellous type and adapted specifically for engaging bone and can include a chamfer and series of notches even at their leading edges to facilitate ease of advancement and self-tapping. Leading portion LP threads 26 can be self-drilling such that leading portion LP can be driven directly into material such as bone without requiring pre-drilling of a hole therefor. When compression screw 10 is used for compressing bone, threads 28 do not need to be adapted for engaging bone since threads 28 can preferably be of a smaller major diameter and pitch diameter than threads 26 and are specifically designed for receiving secondary screw as described herein. Compression screw apparatus 10 according to this invention could also be configured such that the lead of the various threads could be of other relative amounts, as described below.

Figure 4:
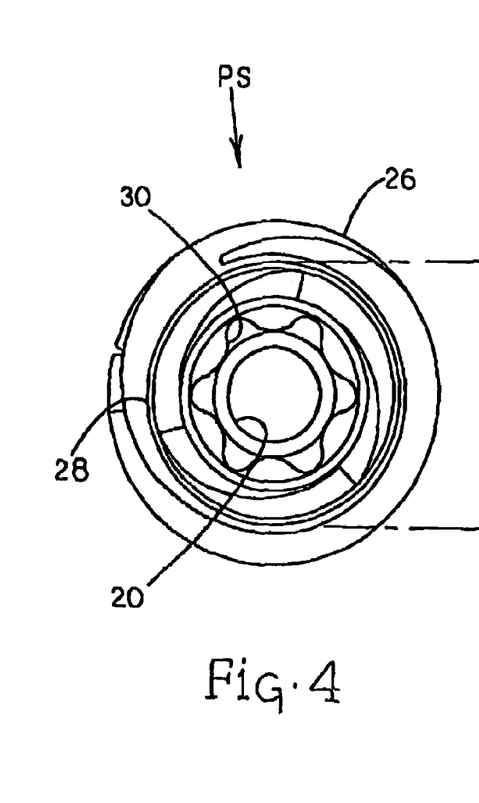
FIG. 4 of the drawings is an end view of the primary screw of the compression screw apparatus illustrating a recess adapted for engagement by a driver.
Figure 6A:
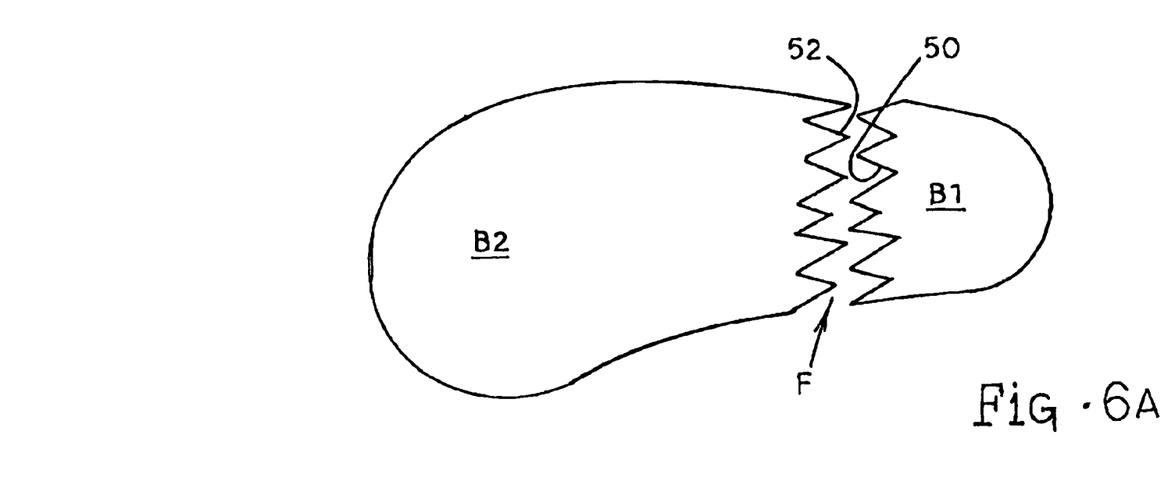
FIGS. 6A-6H of the drawings illustrates exemplary steps when the compression screw apparatus is utilized in a surgical procedure for compression of bone fragments across a fracture line.
Figure 6B:
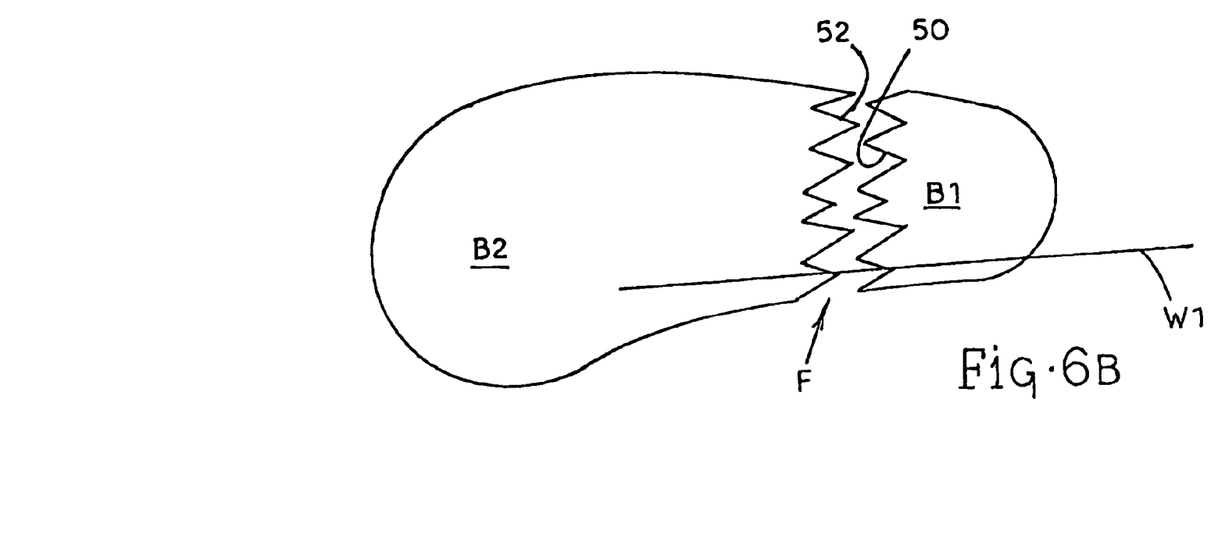
Figure 6C:
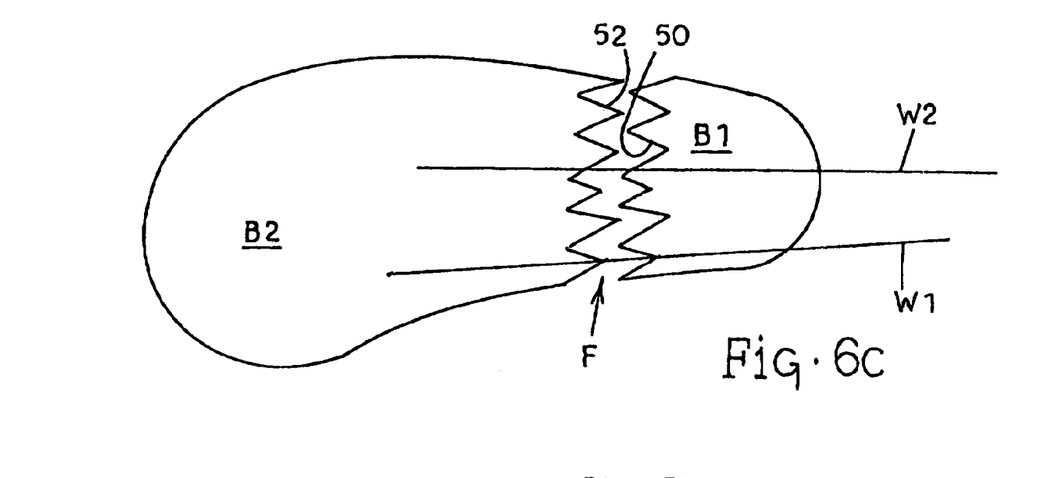
Figure 6D:
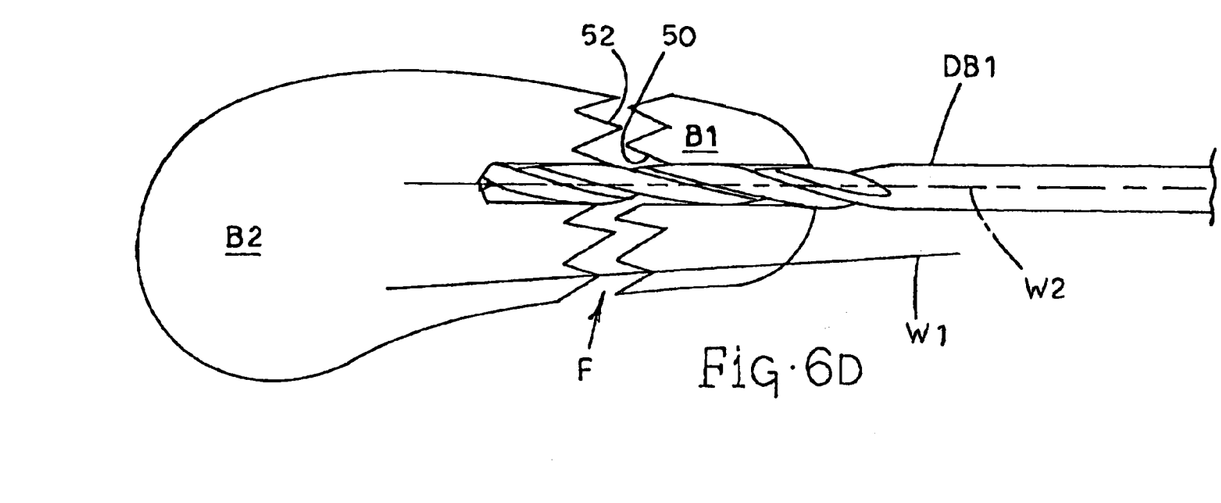
Figure 6E:
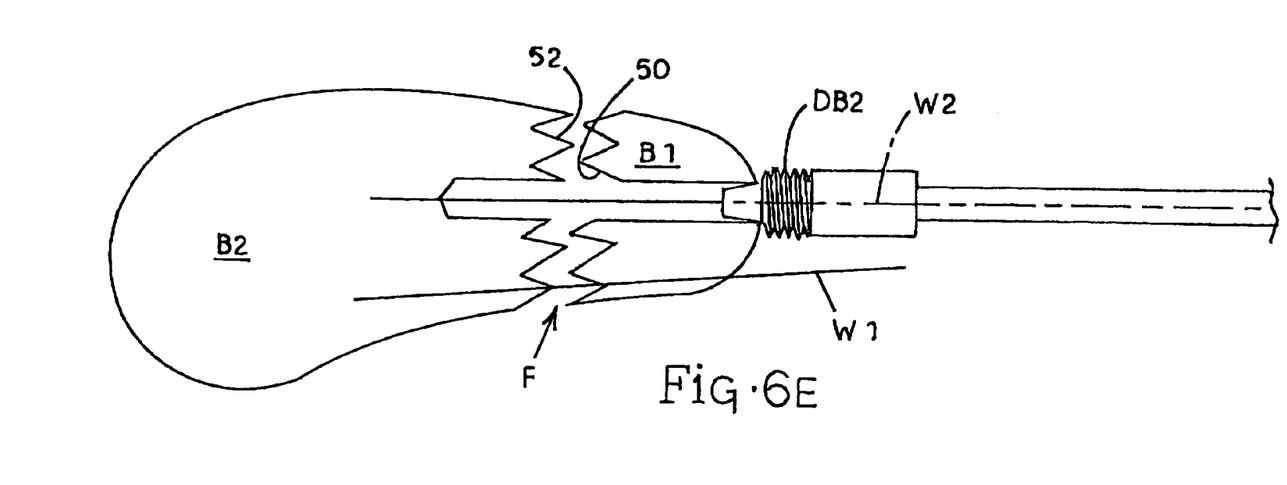
Figure 6F:
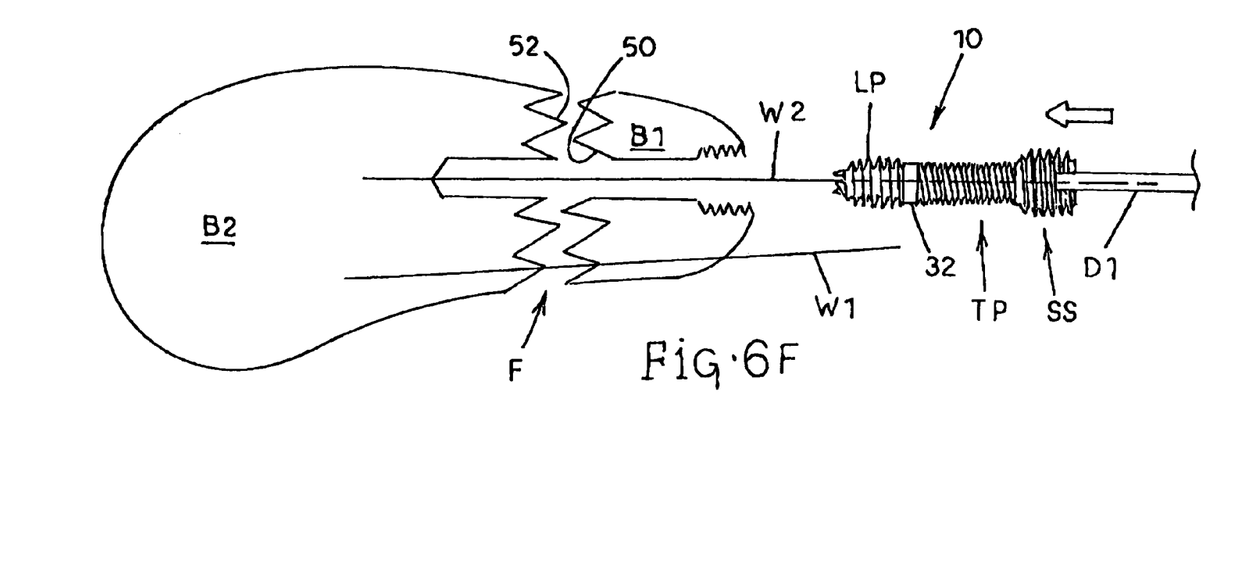

Trailing end 24 of trailing portion TP preferably defines a recessed opening 30 configured to be engaged by a suitably configured driver, such as for example driver D1 shown in FIG. 6F, in order to drive and rotate primary screw PS as it is screwed into bone during use as described herein. The end view of trailing end 24 of primary screw PS illustrated in FIG. 4 shows recessed opening 30 in a hex configuration which can be engaged by driver D1 in order to appropriately drive and screw into place primary screw PS. The configuration of recessed opening 30 could be of any other suitable configuration and match any correspondingly suitable configuration for the head of driver D1, as known to those of skill in the art of screw and driver apparatuses. For example, the configuration of recessed opening 30 could be of a standard hex as shown, hexalobular (Torx or Torx plus), cruciform or other desired shape with the driving head of driver D1 being of a correspondingly matching shape.

As an optional feature, primary screw PS between leading portion LP and trailing portion TP can include a transition portion 32 where the outer surface of primary screw PS can be smooth and unthreaded. When this feature is included as shown in the drawings, transition portion 32 provides a smooth section of compression screw apparatus 10 which can facilitate compression of bone fragments where the bone fragments meet at a compressed fracture line at or proximate transition portion 32. The length of transition portion can extend for any suitable length, and preferably less than approximately 10% or even 5% of the entire length of the primary screw. The diameter of transition portion 32 can be equal to the major diameter of threads 28 of trailing portion TP and smaller than the major diameter of threads 26 of leading portion LP as shown best in FIGS. 1 and 2. It is also envisioned that transition portion 32 could have any other suitable diameter such as a diameter larger or even smaller than the major diameter of threads 26. It is also possible as mentioned above for transition portion 32 to not be present at all on primary screw PS, in which case threads 26 simply are immediately next to threads 28. The presence of an unthreaded transition portion 32 is not functionally required and can especially be excluded where the major diameter of threads 26 is the same or substantially the same as the diameter of the portion of threads 28 adjacent threads 26.

Secondary screw SS of compression screw apparatus 10 preferably comprises an at least generally cylindrical shaped, sleeve-like screw portion for screwing onto primary screw PS. Secondary screw SS defines a threaded central opening CO along its central axis such that secondary screw SS can be screwed onto trailing portion TP of primary screw PS as helical inner threads 34 of secondary screw SS can matingly engage and screw onto threads 28 of trailing portion TP of primary screw PS.

Trailing portion TP of primary screw PS can be straight or slightly tapered, such as at a four(4)-degree or any other suitable angle, so that the diameter of trailing portion TP gradually decreases along the axial length of primary screw PS from transition portion 32 to trailing end 24. When trailing portion TP is tapered in this manner, threaded central opening CO of secondary screw SS can also preferably be appropriately tapered so that threaded central opening CO gradually increases in inner diameter toward its end adapted for first advancing onto primary screw PS. This configuration allows secondary screw SS to screw onto primary screw PS with a locking engagement.

The outer surface of secondary screw SS is at least partially threaded, and preferably can be substantially or even entirely threaded such as by outer helical threads 36 as illustrated in FIGS. 1, 2 and 3. Threads 36 preferably are of a larger major diameter than threads 26 of leading portion LP of primary screw PS, but of the same pitch and lead as threads 26. This preferred relative configuration advantageously ensures that no compression occurs upon insertion of primary screw PS of compression screw apparatus 10 and allows threads 36 of secondary screw SS to create maximum engagement with bone that has substantially been undisturbed. Threads 36 can spiral in the same direction or hand as threads 26 and 28 or primary screw PS. The outer, major diameter of secondary screw SS with threads 36 can be of a constant major diameter on secondary screw SS as shown in the drawings in order to provide the ability to disengage or back out compression screw apparatus 10 as needed without loss of bone engagement. The initial portion of threads 36 which are advanced first onto primary screw PS can, however, slightly taper somewhat similar to threads 26 of leading portion LP, as shown in FIGS. 1, 2, and 3. Additionally, secondary screw SS can also have a tapered outer diameter such that the diameter of secondary screw SS decreases gradually toward the initial portion of threads 36 which are advanced first onto primary screw PS. In this configuration, threads 36 would also have a major diameter that decreases gradually toward the initial portion of threads 36 which are advanced first onto primary screw PS.

In order to be able to provide the desired compression as described further hereinbelow, inner threads 34 of secondary screw SS are preferably of a lead that is larger than the lead of outer threads 36 of secondary screw SS. The lead of inner threads 34 will in a preferred embodiment therefore also be larger than the lead of threads 26 of primary screw since threads 26 preferably have a lead that is at least substantially identical to that of threads 36 of secondary screw SS. The pitch of inner threads 34 of secondary screw SS can therefore be smaller than the pitch of outer threads 36 of secondary screw SS, which can in turn be substantially equivalent to the pitch of leading portion LP.

As can be appreciated by those of skill in the art, relative dimensions and characteristics of threads 26 of leading portion LP, threads 28 of trailing portion TP, inner threads 34 of secondary screw SS, and outer threads 36 of secondary screw SS can be as described above and can also suitably vary. For example, the pitch and lead of threads 26 can be equal or substantially equal to the pitch and lead of threads 36. The pitch of threads 28 can also be the same or substantially the same as the pitch of threads 34. The pitch of threads 28 can be less than the pitch of threads 26, and the lead of threads 26 can be less than the lead of threads 28. With this configuration, compression screw 10 can be inserted by driveably rotating primary screw PS without causing compression of the materials, such as bone fragments, until secondary screw SS is screwed into place after proper positioning of primary screw PS.

It is also envisioned that the configuration and characteristics of the various threads 26, 28, 34 and 36 could be such that the lead of threads 36 can be less than the lead of threads 26, the lead of threads 36 can be less than the lead of threads 28, and the lead of threads 28 can be larger than the lead of threads 36. In this configuration, compression could occur between two pieces of material such as bone even during insertion of compression screw 10.

Figure 6G:
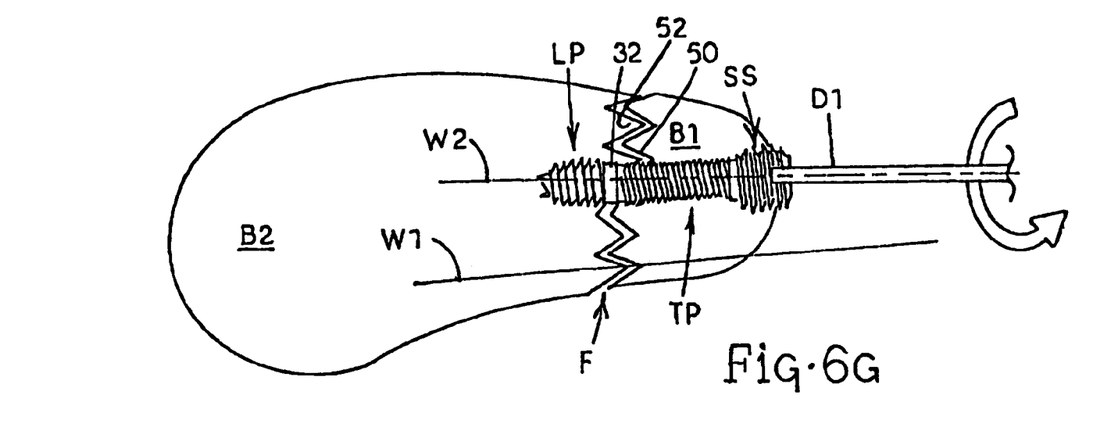
Figure 6H:
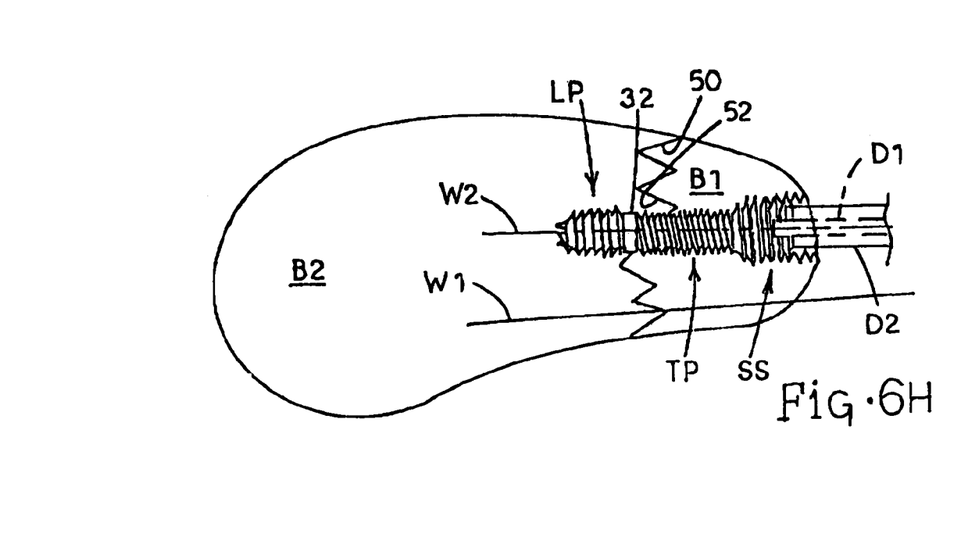

Secondary screw SS can define any suitably configured recess or opening, such as for example slot 38 in an end thereof which is adapted for engagement by a correspondingly suitably configured driver, such as driver D2 shown in FIG. 6H, which can be a cannulated driver that can slideably fit onto and around driver D1. As can be appreciated by those of skill in the art, primary screw PS can advantageously be rotatably driven or even held in place by driver D1 engaging recessed opening 30 even while driver D2 engages slot 38 of secondary screw SS to controllably rotate or hold in place secondary screw SS.

Primary screw PS and secondary screw SS can be constructed of any material suitable for compression of bone screw as described herein and as known to those of skill in the art of orthopedic implants. Particularly suitable materials for construction of primary screw PS and secondary screw SS include, for example, surgical implantable material such as titanium or titanium alloys or stainless steel. It is also envisioned that resorbable materials could be utilized.

Referring now to FIGS. 6A-6H of the drawings, exemplary steps are illustrated which are involved in compression of broken or fractured objects utilizing compression screw apparatus 10. While FIGS. 6A-6H illustrate the broken or fractured objects as proximal and distal bone fragments B1 and B2, respectively, compression screw apparatus 10 can be used for compression of any suitable objects even other than bone fragments B1 and B2, such as, for example, wood or metal objects utilized in woodworking or metal working, respectively.

FIG. 6A illustrates bone fragments B1 and B2 with edges 50 and 52, respectively, spaced apart along a fracture line, generally designated F. While any suitable steps known to those of skill in the art of orthopedic implants can be utilized to install compression screw apparatus 10 and utilize it for compression of two spaced-apart objects, the steps described hereinbelow can in a preferred embodiment be utilized for installation and utilization of compression screw 10.

Initially and as illustrated in FIG. 6B, a wire such as guide wire W can be driven through bone fragment B1 across fracture line F and into bone fragment B2 in order to provide appropriate orientation and stability to the fracture line in preparation for installation of compression screw 10 as described below. Guide wire W1 can be a Kirschner wire, also known as a K-wire in the field of orthopedic implants. After placement of guide wire W1, guide wire W2 can be driven through bone fragment B1, across fracture line F and into bone fragment B2 at a location where compression screw apparatus 10 will be installed.

Drill bit DB1, as shown in FIG. 6D, can then be used to drill through bone fragment B1, across fracture line F, and into bone fragment B2. Drill bit DB1 preferably is cannulated to fit over wire W2 and of a diameter suitable for pre-drilling a hole into which primary screw PS of compression screw apparatus 10 can be screwed. A second drill bit DB2, as shown in FIG. 6E, also is preferably cannulated to fit over wire W2 and can be used to drill into bone fragment B1 in order to pre-drill a hole into which secondary screw SS of compression screw apparatus 10 can be screwed. Drill bit DB2, as shown in FIG. 6E, is preferably of a larger diameter than drill bit DB1 shown in FIG. 6D. As known to those of skill in the art of orthopedic implants, the cannulation of drill bits DB1 and DB2 when used with guide wire W2 facilitate proper positioning of drill bits DB1 and DB2 during use.

Figure 5:
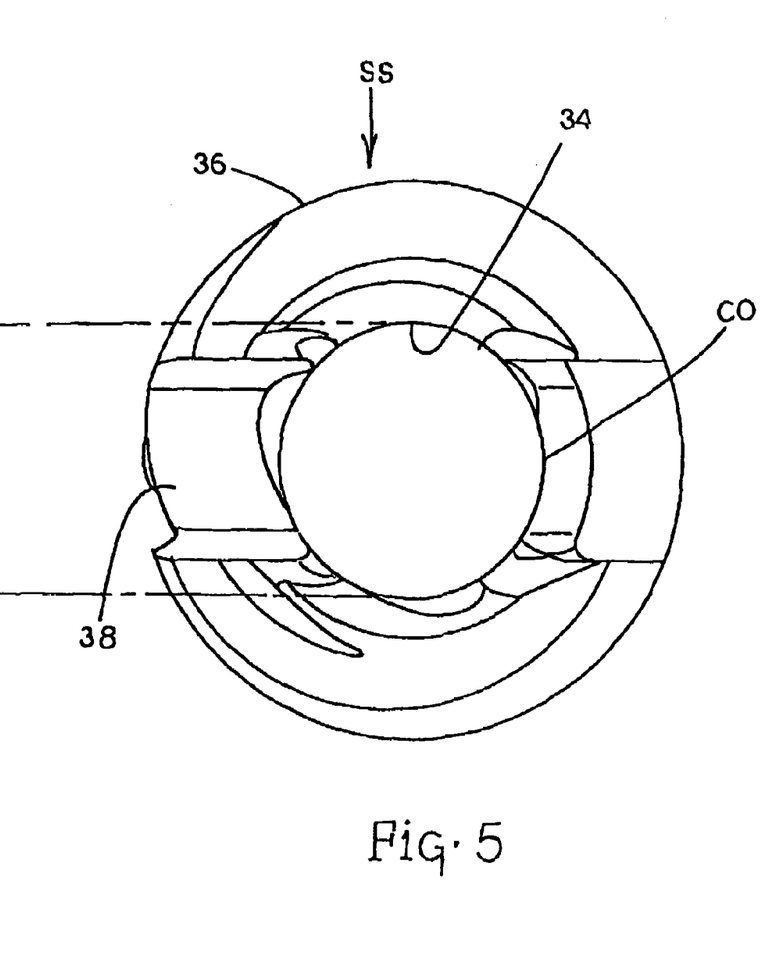
FIG. 5 of the drawings is an end view of the secondary screw of the compression screw apparatus illustrating a slot adapted for engagement by a driver.

Similar to the placement of drill bits DB1 and DB2 over guide wire W2, compression screw apparatus 10 as shown in FIG. 6F can now be placed and is slideable upon guide wire W2 for proper positioning of compression screw apparatus 10 for installation into the predrilled holes. Since the suitably configured recessed opening 30 (shown best in FIG. 4) of trailing portion TP of primary screw PS can be engaged by a suitable driver of a configuration adapted for rotatably screwing primary screw PS even through central opening CO (best shown in FIG. 5) of secondary screw SS, compression screw 10 as shown in FIG. 6F can be placed onto guide wire W2 as a unit with secondary screw SS already screwed at least partially onto trailing portion TP of primary screw PS. As shown in FIG. 6F, cannulated driver D1 is positioned on wire W2 and passes through a portion of central opening CO of secondary screw SS to engage primary screw PS.

As illustrated in FIG. 6G, once compression screw apparatus 10 has been placed appropriately upon guide wire W2, compression screw apparatus 10 can be rotatably driven and screwed by driver D1 into the holes predrilled into bone fragments B1 and B2 by drill bit DB1 and DB2. Wire W1 particularly provides stability during this step, and wire W2 continues to facilitate proper positioning and placement of compression screw 10. As shown in FIG. 6G, leading end 22 of leading portion LP of primary screw PS has been screwed into bone fragment B2 the entire extent of the pre-drilled hole to firmly engage bone fragment B2, while secondary screw SS is still sticking partially above the surface of bone fragment B1. Transition portion 32 can preferably be positioned between or proximate fracture line F of bone fragments B1 and B2.

Referring now to FIG. 6H, secondary screw SS is screwed in and tightened by driver D2 for completion of placement of compression screw 10. This tightening by driver D1 can occur with driver D2 still engaging primary screw PS to hold it in position as illustrated in FIG. 6H or after driver D1 has already been pulled out from engagement with primary screw PS. Tightening of secondary screw SS causes compression of bone fragments B1 and B2 so that they come together at fracture line F, preferably along or at least proximate transition portion 32. Secondary screw SS can be tightened so that it is entirely below the surface of bone fragment B1 with no portion sticking above the surface of bone fragment B1. A substantially constant major diameter of threads 36 can allow for secondary screw SS to be inserted with no portion or head-like structure sticking out. At this point, wire W2 can be withdrawn. As may be necessary, the entire compression screw 10 can be withdrawn from this position by reversing the steps as described.

It will be understood that various details of the disclosed subject matter may be changed without departing from the scope of the subject matter. Furthermore, the foregoing description is for the purpose of illustration only, and not for the purpose of limitation.

What is claimed is:

1. A compression screw apparatus comprising:
   a) a primary screw having a leading end and an opposite trailing end, the primary screw having a lead portion configured for screwing into bone and the lead portion having an outer surface that is at least partially threaded and a trailing portion with a continuous outer surface that is at least partially threaded;
   b) a secondary screw having an outer surface that is at least partially threaded, the secondary screw defining a central opening with an inner surface that is at least partially threaded, the inner threaded surface being configured for mating engagement on the threaded trailing portion of the primary screw such that rotation of the secondary screw relative to the primary screw causes the translation of the secondary screw relative to the primary screw along the threaded trailing portion of the primary screw;
   c.) wherein the threads of the lead portion of the primary screw and the threads of the outer surface of the secondary screw are of at least substantially identical lead; and
   d.) wherein the threads of the trailing portion of the primary screw taper at least partially with a gradually decreasing diameter toward the trailing end of the primary screw.

2. A compression screw apparatus comprising:
   c) a primary screw having a leading end and an opposite trailing end, the primary screw having a lead portion configured for screwing into bone and the lead portion having an outer surface that is at least partially threaded and a trailing portion with a continuous outer surface that is at least partially threaded;
   d) a secondary screw having an outer surface that is at least partially threaded, the secondary screw defining a central opening with an inner surface that is at least partially threaded, the inner threaded surface being configured for mating engagement on the threaded trailing portion of the primary screw such that rotation of the secondary screw relative to the primary screw causes the translation of the secondary screw relative to the primary screw along the threaded trailing portion of the primary screw;
   c.) wherein the threads of the lead portion of the primary screw and the threads of the outer surface of the secondary screw are of at least substantially identical lead; and
   d.) wherein the trailing portion has a diameter that gradually decreases toward the trailing end.

3. The compression screw apparatus of claim 2 wherein the central opening of the secondary screw is of a diameter that increases toward an end of the secondary screw adapted for advancing first onto the trailing portion of the primary screw.

4. A compression screw apparatus comprising:
   a) a cannulated, at least generally cylindrical primary screw having a lead portion terminating in a leading end and a trailing portion terminating in a trailing end, the lead portion having an outer surface that is at least partially threaded and the trailing portion having a continuous outer surface that is at least partially threaded, the trailing portion of the primary screw having a diameter that decreases toward the trailing end; and
   b) an at least generally cylindrical secondary screw having an outer surface that is at least partially threaded with outer threads, the secondary screw defining a central opening with an inner surface that is at least partially threaded with inner threads, the central opening having an inner diameter that increases axially along a length of the secondary screw for mating engagement on the threaded trailing portion of the primary screw such that rotation of the secondary screw relative to the primary screw causes the translation of the secondary screw relative to the primary screw along the threaded trailing portion of the primary screw, wherein the inner threads of the secondary screw are of a larger lead than the outer threads of the secondary screw.

5. The compression screw apparatus of claim 4 wherein the threads of the lead portion of the primary screw and the threads of the outer surface of the secondary screw are of at least substantially identical lead.

6. A compression screw apparatus comprising:
   a) a primary screw having a leading end and an opposite trailing end, the primary screw having a lead portion with an outer surface that is at least partially threaded and a trailing portion with a continuous outer surface that is at least partially threaded;
   b) a secondary screw having an outer surface that is at least partially threaded, the secondary screw defining a central opening with an inner surface that is at least partially threaded, the inner threaded surface being configured for mating engagement on the threaded trailing portion of the primary screw;
   c) wherein the threads of the lead portion of the primary screw and the threads of the outer surface of the secondary screw are of at least substantially identical lead; and
   d) wherein the threads of the trailing portion of the primary screw taper at least partially with a gradually decreasing diameter toward the trailing end of the primary screw.

7. The compression screw apparatus of claim 6 wherein the primary screw is cannulated.

8. The compression screw apparatus of claim 6 wherein the outer surface of the primary screw has a smooth, unthreaded transition portion between the lead portion and the trailing portion of the primary screw.

9. The compression screw apparatus of claim 8 wherein the transition portion extends for less than approximately 5% of an entire length of the primary screw.

10. The compression screw apparatus of claim 6 wherein the threads of the leading portion of the primary screw are of a greater pitch than the threads of the trailing portion.

11. The compression screw apparatus of claim 6 wherein the threads of the leading portion of the primary screw have a deeper root than the threads of the trailing portion.

12. The compression screw apparatus of claim 6 wherein the threads of the leading portion of the primary screw taper with a gradually increasing diameter starting at or proximate the leading end of the primary screw.

13. The compression screw apparatus of claim 6 wherein the trailing end of the primary screw defines a recessed opening.

14. The compression screw apparatus of claim 6 wherein the threads of the leading portion of the primary screw have a greater major diameter than that of the threads outer surface of the secondary screw.

15. The compression screw apparatus of claim 6 wherein the outer threads of the secondary screw are larger in diameter than the threads of the leading portion of the primary screw.

16. The compression screw apparatus of claim 6 wherein the outer threads of the secondary screw are of at least substantially identical pitch as the threads of the leading portion of the primary screw.

17. The compression screw apparatus of claim 6 wherein the outer threads of the secondary screw are of an at least substantially constant major diameter.

18. The compression screw apparatus of claim 6 wherein the threads of the inner surface of the secondary screw are of a larger lead than the threads of the outer surface of the secondary screw.

19. The compression screw apparatus of claim 6 wherein the threads of the primary screw and the threads of the secondary screw are of the same hand.

20. The compression screw apparatus of claim 6 wherein an end of the central opening is adapted for receiving a driver.

21. A compression screw apparatus comprising:
   a) a primary screw having a leading end and an opposite trailing end, the primary screw having a lead portion with an outer surface that is at least partially threaded and a trailing portion with a continuous outer surface that is at least partially threaded;
   b) a secondary screw having an outer surface that is at least partially threaded, the secondary screw defining a central opening with an inner surface that is at least partially threaded, the inner threaded surface being configured for mating engagement on the threaded trailing portion of the primary screw;
   c) wherein the threads of the lead portion of the primary screw and the threads of the outer surface of the secondary screw are of at least substantially identical lead; and
   d) wherein the trailing portion has a diameter that gradually decreases toward the trailing end.

22. The compression screw apparatus of claim 21 wherein the central opening of the secondary screw is of a diameter that increases toward an end of the secondary screw adapted for advancing first onto the trailing portion of the primary screw.

* * * * *